United States Patent
Hersh et al.

(10) Patent No.: US 11,759,308 B2
(45) Date of Patent: Sep. 19, 2023

(54) DEVICES FOR THE AMELIORATION OF AN ABNORMALITY OF A CORNEA AND METHODS OF USING THEM

(71) Applicants: Peter S. Hersh, Teaneck, NJ (US); Steven A. Greenstein, Teaneck, NJ (US); John D. Gelles, Teaneck, NJ (US)

(72) Inventors: Peter S. Hersh, Teaneck, NJ (US); Steven A. Greenstein, Teaneck, NJ (US); John D. Gelles, Teaneck, NJ (US)

(*) Notice: Subject to any disclaimer, the term of this patent is extended or adjusted under 35 U.S.C. 154(b) by 0 days.

(21) Appl. No.: 18/087,424

(22) Filed: Dec. 22, 2022

(65) Prior Publication Data
US 2023/0181309 A1    Jun. 15, 2023

Related U.S. Application Data

(63) Continuation-in-part of application No. PCT/US2022/036042, filed on Jul. 2, 2022, which is a continuation-in-part of application No. 17/528,484, filed on Nov. 17, 2021, now Pat. No. 11,406,531.

(Continued)

(51) Int. Cl.
*A61F 2/14*  (2006.01)
*A61L 27/36*  (2006.01)

(52) U.S. Cl.
CPC .......... *A61F 2/142* (2013.01); *A61L 27/3604* (2013.01); *A61L 2430/16* (2013.01)

(58) Field of Classification Search
CPC .......... A61F 9/0079; A61F 2009/00872; A61F 9/013; A61F 9/007; A61F 2009/00853; A61F 9/008; A61F 2009/00882; A61F 2009/00893; A61F 9/00834; A61F 2/147; A61F 9/00804; A61F 9/009; A61F 2/142; A61F 2009/0088; A61F 2009/00895; A61F 9/0017; A61F 9/00812; A61F 2009/00844; A61F 2009/00851; A61F 2009/00855; A61F 2009/00863; A61F 2009/0087; A61F 2009/00887; A61F 9/00802; A61F 9/00806; A61F 9/00817; A61F 9/00821; A61F 9/00827; A61B 3/107; A61B 18/1815; A61B 18/18; A61B 3/0025; A61B 18/14; A61B 2018/00005; A61B 2018/00029; A61B 2018/00755; A61B 2018/00875;

(Continued)

(56) References Cited

U.S. PATENT DOCUMENTS

8,394,140 B2 * 3/2013 Chapoy .................. A61F 2/147
                                                        623/5.11
8,409,177 B1    4/2013 Lai
(Continued)

*Primary Examiner* — Brandi N Thomas
(74) *Attorney, Agent, or Firm* — RosserIP, LLC; Roy Rosser (57) ABSTRACT

Corneal augmentations designed for the amelioration of an abnormality of a cornea and methods of using them are disclosed. The corneal augmentations are shaped from corneal templates. The required arcuate 3-D shapes of the corneal augmentations are determined based on elevation maps of the cornea as well as measurements of a severity of the abnormality such as the maximum keratoconus, K-max. Shaping of the corneal augmentation is done using computer-controlled femtosecond lasers and laser ablation.

20 Claims, 9 Drawing Sheets

Related U.S. Application Data

(60) Provisional application No. 63/397,553, filed on Aug. 12, 2022, provisional application No. 63/225,484, filed on Jul. 24, 2021.

(58) Field of Classification Search
CPC . A61B 2090/065; A61B 3/1005; A61B 34/10; A61B 5/1078; A61B 17/085; A61B 18/082; A61B 18/20; A61B 2017/306; A61B 2017/320052; A61B 2018/00011; A61B 2018/00636; A61B 3/0066; A61B 3/10; A61B 3/1015; A61B 3/102; A61B 3/12; A61B 3/13
See application file for complete search history.

(56) References Cited

U.S. PATENT DOCUMENTS

| | | | |
|---|---|---|---|
| 9,931,199 B2 | 4/2018 | Albertazzi | |
| 2017/0319329 A1* | 11/2017 | Muller | A61F 2/145 |
| 2022/0079743 A1 | 3/2022 | Jacob | |
| 2022/0110738 A1 | 4/2022 | Kilic | |

* cited by examiner

Cross-sections on "CC"

DEVICES FOR THE AMELIORATION OF AN ABNORMALITY OF A CORNEA AND METHODS OF USING THEM

CROSS-REFERENCE TO RELATED APPLICATIONS

This is a US continuation application of International Application PCT/US22/36042 with an international filing date of Jul. 2, 2022, that claims priority to U.S. patent application Ser. No. 17/528,484 filed on Nov. 17, 2021, and issued as U.S. Pat. No. 11,406,531 on Aug. 9, 2022, and which in turn claims priority to U.S. provisional patent application No. 63/225,484 that was filed on 24 Jul. 2021, the contents of all of which are hereby incorporated by reference. The application also claims priority to U.S. provisional patent application No. 63/397,553 that was filed on Aug. 12, 2022, the contents of which are hereby fully incorporated by reference.

BACKGROUND OF THE INVENTION

(1) Field of the Invention

The invention relates to medical devices and methods for the amelioration of abnormalities of the cornea and more particularly to the production and/or use of corneal augmentations that may be used either as inlays or onlays to ameliorate abnormalities of the cornea such as, but not limited to, keratoconus.

(2) Description of Related Art

The most common corneal disorder is corneal ectasia which occurs as a result of the thinning and subsequent distortion of the cornea. This distortion alters the normal optical anatomy of the cornea and decreases vision. Corneal ectasia may have several causes and may manifest as a condition such as, but not limited to, keratoconus, pellucid marginal degeneration and keratoglobus. Corneal ectasia may also be iatrogenic in nature resulting from various surgeries such as, but not limited to, laser-assisted in-situ keratomileusis (LASIK), small incision lenticule extraction (SMILE), and photorefractive keratectomy (PRK).

The most common natural manifestation of corneal ectasia is keratoconus, a condition that occurs in approximately 1 in 2000 individuals. This is an asymmetric corneal ectatic disorder characterized by progressive corneal protrusion and thinning, typically causing irregular astigmatism and impaired visual function. In particular, the normally dome, or spherically, shaped cornea becomes distorted resulting in the formation of a cone shaped bulge. This cone shaped protrusion typically adversely affects vision.

Devices and methods for ameliorating corneal ectasia depend on the type and severity of the condition and include treatments such as, but not limited to contact lenses, intra corneal implants, cross-linking, and corneal transplants.

Intra-corneal implants include intrastromal corneal ring segments (ICRS) made of materials such as, but not limited to, PMMA. In the US, these are often referred as Intacs®, which is the tradename of the devices produced by Addition Technology, Inc. of Lombard Ill., a subsidiary of AJL Ophthalmic, a Spanish company headquartered in Minano, Alva, Spain. One shortcoming of such inserts is that almost all suitable materials have a refractive index significantly greater than the 1.376 refractive index of the stromal collagen of the cornea. This mismatch can result in unwanted reflective surfaces that may interfere with vision. Additional complications that may arise from a lack of biocompatibility include stromal melting and segment extrusion. Moreover, the commercially available ring segments are currently fixed in arc length, width, inner and outer diameter. The only variable is the thickness; thus, the devices are not customizable to any great degree of precision.

Work has been reported on stromal lenticule addition keratoplasty (SLAK) in which patients with advanced keratoconus underwent implantation with a negative meniscus shaped intrastromal lenticule into a pocket within their corneal stroma. This procedure is discussed in, for instance, the article "Epithelial and stromal remodelling following femtosecond laser— assisted stromal lenticule addition keratoplasty (SLAK) for keratoconus" by Nubile et al., Sci Rep 11, 2293 (2021) the contents of which are hereby incorporated by reference.

However, limited work has been done on optimizing the shape of the intrastromal corneal implants to most appropriately ameliorate the various ectatic corneal disorders.

The Relevant Prior Art Includes:

U.S. Pat. No. 8,409,177 granted to Lai Apr. 2, 2013, entitled "Intrastromal refractive surgery by inducing shape change of the cornea". The pattern specification describes using a laser-ablation created intrastromal pocket which may be filled with a polymerizable fluid that is then cured.

Biocompatible polymerizable fluids typically also have an index of refraction significantly more the 1.376 typical of the cornea. The mismatched refractive indices may result in unwanted reflections and local focusing or defocusing that may interfere with vision.

U.S. Pat. No. 9,931,199 granted to Albertazzi on Apr. 3, 2018, entitled "Methods and apparatus for treating keratoconus" that describes a processing module that uses eye topography data to provide a surgical plan based on existing manufacture's available intrastromal corneal ring segments (ICRS).

US Patent Application 20220079743 submitted by Jacob; Soosan on Mar. 17, 2022 entitled "Shaped Corneal Segments: Corneal Allogenic Intra-Stromal Devices (Ring Segments And Rings, Modified Discs, Modifications) for Inducing Shape Change, Regularization and Stabilization of Cornea in Corneal Ectasia And Other Corneal Conditions And For Correction Of Refractive Errors" that describes a device for implantation into the cornea intra-stromally comprising allogenic corneal or scleral material or other bioengineered material including, but not limited to, processed collagen tissues, comprises a segment that is inserted into a corneal channel whereby the segment regularizes the conical cornea, gives an improved surface, improves biomechanical strength distribution and stability improves optical functionality, and improves/corrects the refractive error or gives other desired shape change effects.

US Patent Application 20220110738 filed by Kilic; Aylin on Apr. 14, 2022 entitled "Methods and Materials for Modifying Corneal Shape" that describes that modifying corneal shape involves implantation of a segment of tissue in the corneal stroma, where the properties of the tissue segment and its anatomical placement provide a change in corneal topography. In particular, such methods and materials can be used for correction of defects in corneal shape, such as corneal ectasias.

Various implementations are known in the art, but fail to address all of the problems solved by the invention described herein. Various embodiments of this invention are illustrated in the accompanying drawings and will be described in more detail herein below.

BRIEF SUMMARY OF THE INVENTION

Inventive devices for the amelioration of an abnormality of a cornea and method of using them are disclosed. Corneal abnormalities, such as, but not limited to, ectatic disorders, may be a result of the thinning of the cornea that may become distorted and, therefore, adversely affect a patient's vision. Abnormalities include diagnosis such as, but not limited to, keratoglobus, pellucid marginal degeneration, keratoconus, and forms of astigmatism, including irregular astigmatism. Additionally, these templates may be customized to augment other abnormal or irregular corneal shapes such as iatrogenic irregular corneas such as after corneal surgery, such as, but not limited to, after penetrating keratoplasty, anterior lamellar keratoplasy, LASIK, PRK, SMILE, irregularity induced by corneal trauma, irregularity induced by disease such as ulceration.

As part of an assessment of the structure and severity of a patient's disorder, one or more corneal maps of the patent's cornea may be obtained. These maps may be, but are not limited to, tomographic, topographic, or elevation maps, or some combination thereof. These maps may be used, for instance, to locate a cone of a keratoconus, and, to quantify metrics of corneal asymmetry and severity, such as but not limited to maximum keratometry of the patient's cornea.

In a preferred embodiment, the corneal maps of a patient exhibiting an ectatic or irregular disorder may be created using methods such as, but not limited to, computerized corneal topography, corneal tomography, or other forms of modeling. The information derived from these maps, such as, but not limited to, the maximum keratometry, landmark location and elevations, and various iso-deviation contours, may then be used to calculate an appropriate three-dimensional shape of a corneal augmentation suitable for ameliorating the ectatic or irregular disorder. The ideal shape of the corneal augmentation may, for instance, be one that restores the patient's cornea to an ideal cornea, i.e., a portion of spheroid having a refractive power in the range of 30 to 50 diopters with an eccentricity ranging from −2 to +2.

A corneal template may be obtained as, for instance, a corneal autograft, a corneal allograft, a corneal xenograft, manufactured corneal tissue, bioengineered corneal tissue, or some combination thereof. The template may for instance be made of materials that either mimic the properties of corneal tissue, or have properties that are analogous to corneal tissue. They may, for instance, be constructed or engineered from pure collagen that has been subjected to treatments such as, but not limited to, chemical cross-linking or photochemical crosslinking.

This corneal template may be treated for a number of purposes such as, but not limited to, to improve its biocompatibility, to maintain its clarity, and to increase its biomechanical strength.

This corneal template may be formed into a device that is a corneal augmentation having the desired three-dimensional shape. This may be accomplished using, for instance, a computer guided femtosecond or an excimer laser, or a combination thereof.

The corneal augmentation may then be used to augment the cornea either as an inlay or as an overlaying.

When the corneal augmentation is an inlay, a patient's cornea exhibiting an ectatic disorder may be prepared to receive the corneal augmentation by creating an intra-corneal cavity using, for instance, a femtosecond laser. The intra-corneal cavity may be a space such as, but not limited to, a channel or a pocket with an appropriate opening for insertion of the augmentation. The corneal augmentation may then be inserted into the intra-corneal cavity, thereby augmenting the patient's cornea, and altering the corneal shape, thickness and biomechanics.

When the corneal augmentation is an onlay, the patient's cornea exhibiting an ectatic disorder may be prepared by first removing a region of epithelial tissue from the cornea. In one embodiment, the augmentation may be laid in a desired position on the de-epithelialized cornea surface. The tissue may be held in place by the corneal-endothelial suction force, in a manner similar to a LASIK flap. In a further embodiment, a surface chamfer, having the shape of the periphery of the augmentation, may then be created on the de-epithelialized corneal surface, using, for instance, a femtosecond laser. The corneal augmentation may then be augmented onto the patient's cornea and initially held in place by, for instance, inserting a tapered, or chamfered, edge of the corneal augmentation into the chamfer of the corneal tissue. This may maintain the onlay in place while the epithelial tissue grows over the onlay. Surgical glues or sutures may also or instead be used for this temporary holding. Epithelial regrowth may take a few days to a week, during which time the patient's cornea may be protected by a surgical contact lens. Once in place, the onlay may improve the patient's corneal shape, thickness, and biomechanics. Alteration of the corneal shape, thickness, and biomechanics may result in aberration changes.

When the inlay and onlay corneal augmentations are put in place, they may themselves be sufficient to ameliorate the abnormality, or ectatic corneal disorder. However, they may also or instead be a first step, and may be followed by a post-augmentation further reshaping of the cornea or the corneal augmentation. The post-operative further reshaping of the corneal augmentation may, for instance, be a surgery mediated by laser, such as, but not limited to, an excimer or femtosecond laser, in the form of a surface or intrastromal modification.

DETAILED DESCRIPTION OF THE INVENTION

The preferred embodiments of the present invention will now be described with reference to the drawings. Identical elements in the various figures are identified, in so far as possible, with the same reference numerals. The embodiments that are described in detail are provided by way of explanation of the present invention, which is not intended to be limited thereto. In fact, those of ordinary skill in the art may appreciate upon reading the present specification and viewing the present drawings that various modifications and variations can be made thereto.

Figure 1:
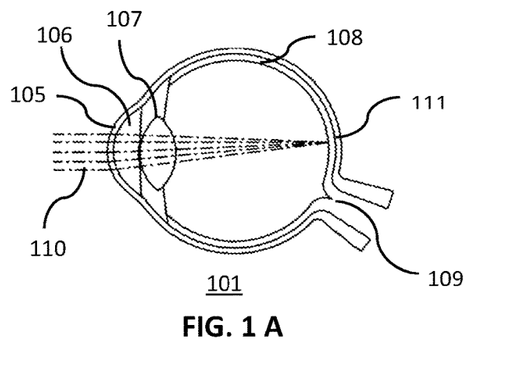
FIG. 1A shows a schematic cross-section of a normally functioning human eye.
FIG. 1B shows a schematic cross-section of an eye exhibiting an abnormality of the cornea.

FIG. 1A shows a schematic cross-section of a normally functioning eye.

In a normally functioning human eye, an incoming, parallel beam of light 110 may be light correctly focused 111 onto the retina 108 by the combined action of a lens 107 and a cornea 105. The image created on the retina 108 may then be transmitted to the brain via the optic nerve 109. The anterior cavity 106 is typically filled with a clear fluid, the aqueous humor, and separates the cornea 105 from the lens 107.

FIG. 1B shows a schematic cross-section of an eye exhibiting an abnormality of the cornea. Corneal ectasia may be caused by the thinning and subsequent distortion of the cornea and may be manifested as a condition such as, but not limited to, keratoconus, pellucid marginal degeneration and keratoglobus. As a consequence of the thinning, the cornea 112 exhibiting an ectatic disorder may be distorted away from the normal spheroidal shape of a healthy cornea, thereby impairing its optical performance. For instance, only a small fraction of an incoming, parallel beam of light 110 may be correctly focused on the retina 108, while the remainder of the light 113 may not be brought to a correct focus on the retina.

Figure 2:
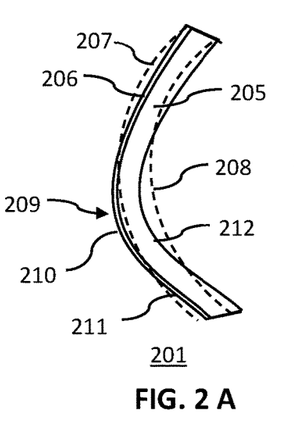
FIG. 2A shows a schematic cross-section of a cornea exhibiting an ectatic disorder.
FIG. 2B shows a schematic cross-section of a cornea having two intra-stromal cavities.
FIG. 2C shows a schematic cross-section of a cornea having intra-stromal collagen augmentations as inlays.

FIG. 2A shows a schematic cross-section of a cornea exhibiting an ectatic disorder.

As shown, the cornea may be exhibiting keratoconus 209 in which a portion of the cornea may assume an irregular optical surface that may sometimes be referred to as a cone. The degree or severity of the keratoconus 209 may be characterized by the deviation of the cornea from an optimal optical structure. Such an optimal optical structure may, for instance, be an ideal cornea, i.e., a portion of spheroid having a refractive power in the range of 30 to 50 diopters with an eccentricity ranging from −2 to +2. The severity of the condition may be quantified by a number of clinical variables. These variables may, for instance, include the following:

1: The maximum keratometry or K-max. This may be measured as the maximum deviation of the cornea from the ideal and may determine the severity of the keratoconus. A measure of the maximum keratometry 210 may, for instance, be obtained using an instrument such as, but not limited to, a Pentacam™ manufactured by OCULUS Optikgerate GmbH in Wetzlar, Germany. The measurement may be quantified in diopters or as a deviation in μm of the anterior surface of the cornea 211 from a best fit sphere 207 for anterior surface of cornea, or as a deviation in μm of the posterior surface of the cornea 212 from a best fit sphere 208 for posterior surface of cornea, or a combination thereof.

2: An estimate of the corneal curvature over the visual axis. This may be obtained from refraction measurements of the degree of myopia and hyperopia caused by the deformed cornea. The myopia may be measured assuming the visual axis passes through the steepest part of the deformed cornea, i.e., the cone of the keratoconus. The hyperopia may be measured by assuming the visual axis passes through the flatter part of the deformed cornea. Both of this refraction measurements may also be calculated from data obtained using corneal tomography or topography as performed by an instrument such as, but not limited to, the aforementioned Pentacam™.

3: The location of the so-called cone of the keratoconus, particularly the location of the cone relative to the pupil. This clinical location may be obtained by overlying a map of the cornea with an iris image. A map of the cornea may show the local focusing power of the cornea and may be obtained with an instrument such as, but not limited to, a Pentacam™. Optical topography and tomography instruments such as the Pentacam™ typically have an iris camera that may provide a suitable iris image.

4: The diameter of the cone on the cornea. This may, for instance, be obtained from an elevation map that may compare the local height of the cornea to a reference surface such as, but not limited to, a best fit sphere. For instance, a best fit sphere 207 for the anterior surface of the cornea may be compared to the anterior surface of the cornea 211 to produce an elevation map. A roughly circular patch may then become apparent as the boundary at which the cornea starts to deviate significantly from the best fit sphere. The diameter of a best fit circle to this region may then be deemed to be the diameter of the cone. The same calculation may be done comparing the posterior surface of the cornea 212 to a best fit sphere 208 for the posterior surface of the cornea.

Based on the clinical measurements of the severity, location and diameter of the keratoconus cone, a clinician may then determine both a best device, or corneal augmentation, and a best course of treatment. The device may be either a corneal inlay or a corneal onlay and the treatment may, for instance, be a multistep treatment in which a corneal inlay or onlay is added to the patent's cornea, followed later by laser reshaping of the thickened cornea.

FIG. 2B shows a schematic cross-section of a cornea having two intra-stromal cavities.

Depending on factors such as, but not limited to, the severity and location of the disorder, a clinician may opt to treat it with a single inlay, or with multiple inlays. The multiple inlays may be of different shapes and sizes.

The intra-stromal cavities 213 and 214 may be created in the corneal stroma 205 using any suitable surgical means though the use of a femtosecond laser may be preferred as the photodissociation incisions produced by a femtosecond laser cause minimal damage to surrounding tissue. The intra-stromal cavities 213 and 214, or pockets, may create a space appropriately sized and shaped to each receive a corneal augmentation. A typical cornea is about 540 µm+/− 30 µm thick though, with ectasia, the thickness in regions may be as little as 300 µm. An optimal depth for locating the intra-stromal cavities may be between 50 µm from the epithelial tissue and at least 50 µm above the posterior surface of the cornea, or Descemet's layer. There may be entrances to the intra-stromal cavities 213 and 214 that pierce the epithelial tissue 206 and allow for the insertion of the corneal augmentations.

FIG. 2C shows a schematic cross-section of a cornea having intra-stromal collagen augmentations as inlays.

The corneal augmentations 216 and 218 may have been placed, or inlayed, into the intra-stromal cavities 213 and 214 thereby ameliorating the keratoconus by strengthening and reshaping the cornea. In particular, both the anterior surface of the cornea 211 and the posterior surface of the cornea 212 may now more closely aligned to the best fit sphere 207 for anterior surface of cornea and the best fit sphere 208 for posterior surface of cornea respectively. The cornea may now more closely approximates an ideal optical structure, thereby improving its optical performance and the patient's vision.

Figure 3:
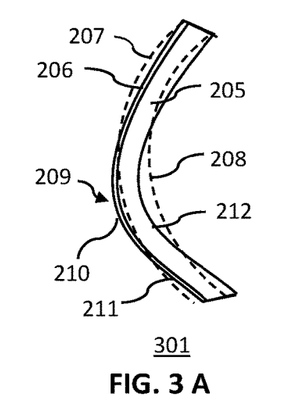
FIG. 3A shows a schematic cross-section of a cornea exhibiting a keratoconus.
FIG. 3B shows a schematic cross-section of a cornea prepared to receive two corneal augmentations as corneal onlays.
FIG. 3C shows a schematic cross-section of a cornea augmented with two corneal augmentations and that may be corneal onlays.
FIG. 3D shows a schematic cross-section of a cornea augmented with two corneal onlays after regrowth of the epithelial tissue.

FIG. 3A shows a schematic cross-section of a cornea exhibiting a keratoconus.

As in FIG. 2A, the cornea may be exhibiting keratoconus 209 having a maximum keratometry 210 in a vicinity of the thinnest part of the corneal stroma 205. The deformation of the cornea may be measured as a deviation of the anterior surface of the cornea 211 from a best fit sphere 207 for anterior surface of cornea. An almost identical pattern may be seen in the deviation of the posterior surface of the cornea 212 from a best fit sphere 208 for posterior surface of cornea. Both these deviations may be mapped and visualized as elevation maps by means of tomography or topography using an instrument such as, but not limited to, the Pentacam™ mentioned above.

FIG. 3B shows a schematic cross-section 302 of a cornea prepared to receive two corneal augmentations as corneal onlays. A first surgical step in the onlay procedure may be to remove one or more regions 305 and 310 of epithelial tissue 206. This removal may be performed by any suitable surgical procedure, but the use of a femtosecond laser may be preferred as the photodissociation incisions produced by a femtosecond laser cause minimal damage to surrounding tissue. The regions 305 and 310 in which epithelial tissue is removed may typically be on either side of the thinnest part of the corneal stroma 205.

In addition to removing the epithelial tissue, a surface chamfer 306 may be produce on a periphery of the region of removed epithelial tissue. This may also be done using a femtosecond laser and may serve to help secure the on-laid corneal augmentation.

FIG. 3C shows a schematic cross-section 303 of a cornea augmented with two corneal augmentations 308 and 311 that may be corneal onlays.

The corneal augmentations 308 and 311 may be corneal onlays that may be placed over, or on-laid, over the regions in which epithelial tissue has been removed. The corneal augmentations may be held in place temporarily by having its outer periphery tucked under a surface chamfer 306 on the periphery of the region of removed epithelial tissue. The corneal augmentation may also or instead be temporarily held in place by surgical glue or sutures, or a combination thereof.

Figures 3, 3D:
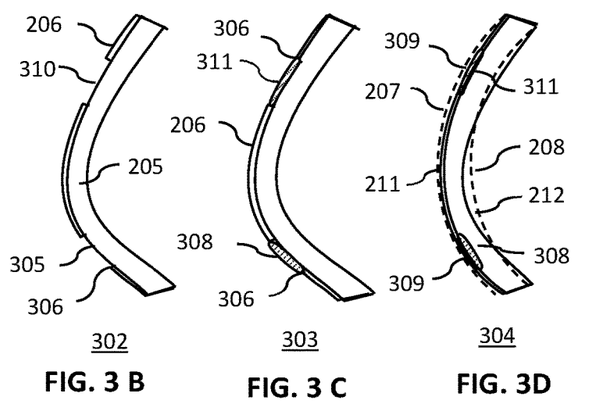

FIG. 3D shows a schematic cross-section 304 of a cornea augmented with two corneal onlays after regrowth of the epithelial tissue 309.

Regrowth of the epithelial tissue may take approximately a few days to a week. During this period a patient may wear surgical contact lenses to protect the augmentation. As the epithelial tissue regrows, the corneal augmentations 308 may integrate with the corneal stroma 205 thereby strengthening and reshaping the cornea. In particular, both the anterior surface of the cornea 211 and the posterior surface of the cornea 212 may now be more closely aligned to the best fit sphere 207 for anterior surface of cornea and the best fit sphere 208 for posterior surface of cornea respectively. The cornea may now more closely approximate an ideal optical structure, thereby ameliorating the keratoconus. This may also improve the cornea's optical performance and the patient's vision.

Although the procedures detailed in FIGS. 2A-C and 3A-D, are shown as having two corneal augmentations each, there are many occasions on which a single suitably shaped and placed corneal augmentation may prove as, or even more, effective in ameliorating the corneal abnormality.

The procedures detailed in FIGS. 2A-C and 3A-D, i.e., augmentation with corneal inlays and corneal onlays, may themselves be sufficient to ameliorate the abnormality, or ectatic corneal disorder. However, they may also or instead be a first step, and may be followed by a post-augmentation further shaping of the corneal augmentation. The post-augmentation further shaping of the corneal augmentation may, for instance, be a surgery such as, but not limited to, a photorefractive keratectomy (PRK) surgery or a phototherapeutic keratectomy (PTK). Such surgeries may, for instance, be accomplished using a suitable laser such as, but not limited to, a femtosecond laser, or an Excimer laser, or a combination thereof.

Figure 4:
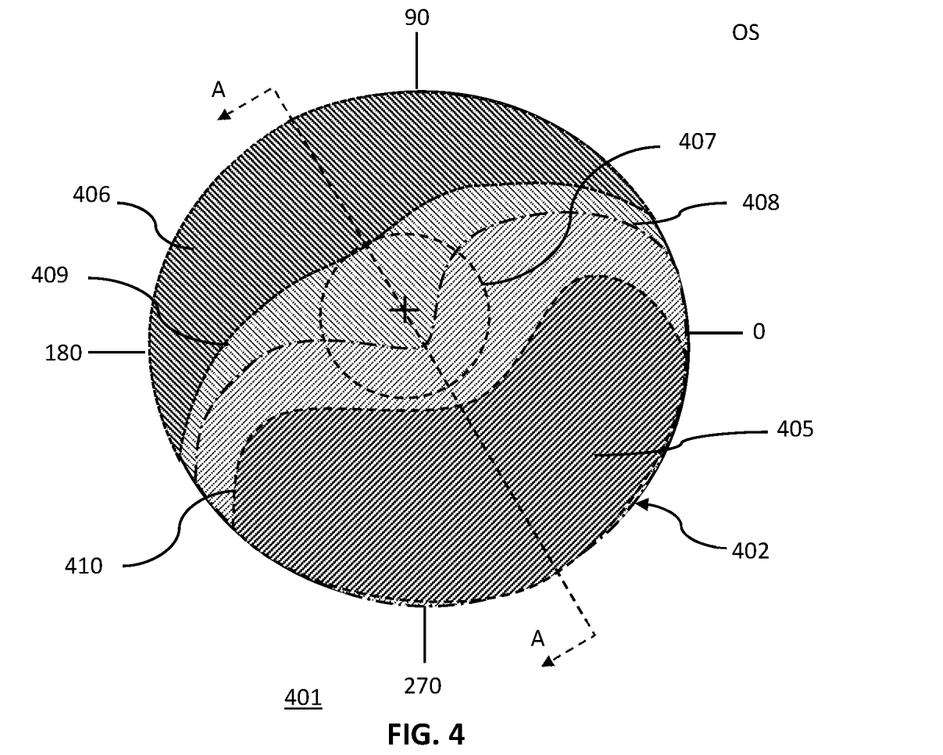
FIG. 4 shows a schematic representation of an elevation map of a cornea.

FIG. 4 shows a schematic representation 401 of an elevation map 402 of a cornea.

The elevation map may represent a comparison of one of the corneal surfaces with respect to a reference surface. The reference surface may, for instance, be an idealized shape of the corneal surface such as, but not limited to, a best fit sphere, an ellipsoid or a toric ellipsoid. Elevation maps may be obtained using instruments such as, but not limited to, a Pentacam™ manufactured by OCULUS Optikgerate GmbH in Wetzlar, Germany.

Elevation maps are typically generated as a grid of numbers representing the deviation in μm of the corneal surface from the reference surface. They are typically displayed in false color, with, by convention, elevated regions shown in warm colors tending to the red end of the spectrum, and depressed regions shown in cold colors tending to the blue end of the spectrum. For simplicity, and to conform to USPTO rules for drawings, the elevation map 402 of FIG. 4 has been drawn showing depressed and elevated regions in different shadings. For instance, the shaded region 405 is intended to represent a region in which an anterior surface of a cornea may be depressed with respect to a best fit sphere. Differently shaded region 406 is intended to represent a region in which an anterior surface of the cornea is elevated with respect to the best fit sphere.

Elevation maps may also display iso-elevation lines. Examples include, but not limited to, iso-elevation line 410 showing a line of constant depression with respect to a best fit sphere; iso-elevation line 409 showing a line of constant elevation with respect to a best fit sphere; and zero deviation iso-elevation line 408 showing a line having zero elevation or depression with respect to the best fit sphere.

The numbers 0, 90, 180 and 270 shown on FIG. 4 represent orientation in degrees as per ophthalmic convention. OS stands for Oculus Sinister, ophthalmic notation for a left eye. OD would represent Oculus Dexter, the right eye. As a point of reference, in normal eyes the anterior elevations, i.e., the deviation of a anterior corneal surface from a best fit sphere, are typically in a range 1.63+/−1.4 μm. In a patient with keratoconus, the anterior elevations may be the range of 20.9+/−21.9 μm. Best fit spheres typically have a radius in a range of 6.5+/−2 mm.

FIG. 4 also shows a circle 407 representing a cone of a keratoconus. This may be a best fit circle to an iso-elevation line at which the surface of the cornea starts to deviate significantly from the best fit sphere. The diameter of a best fit circle may be deemed to be the diameter of the cone of the keratoconus.

Figure 5:
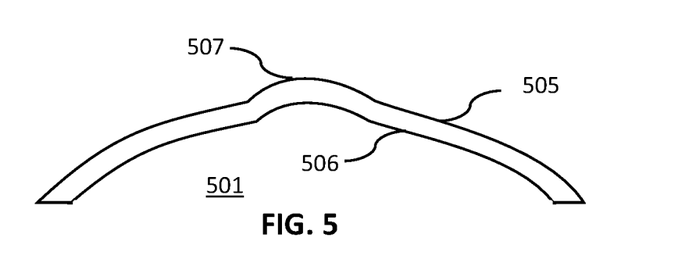
FIG. 5 shows a schematic cross-section taken on "AA" of FIG. 4.

FIG. 5 shows a schematic cross-section 501 taken on "AA" of FIG. 4.

The cross-section shows both an anterior surface 505 of a cornea and a posterior surface 506 of the cornea. The keratoconus 507 may be seen as a deviation of the surfaces of the cornea from an ideal shape such as a best fit sphere.

Figure 6:
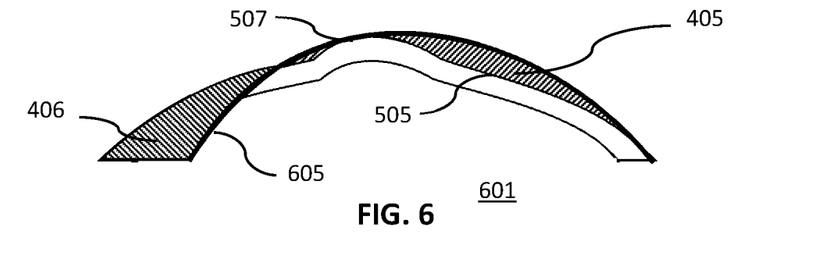
FIG. 6 shows a schematic representation depicting the elevation of an anterior surface of a cornea with respect to a best fit sphere.

FIG. 6 shows a schematic representation 601 depicting the elevation of an anterior surface 505 of a cornea with respect to a best fit sphere 605.

The best fit sphere 605 shown in FIG. 6 may be a best fit sphere relative to the apex of the keratoconus 507. The shaded region 405 depicts where the anterior surface of the cornea is depressed with respect to a best fit sphere, while the shaded region 406 depicts where the anterior surface of the cornea is elevated with respect to a best fit sphere.

The elevation map relative to the apex of the keratoconus may be the most accurate map to demarcate the depressed area of the cornea which may be elevated postoperatively by an inlayed corneal augmentation.

Figure 7:
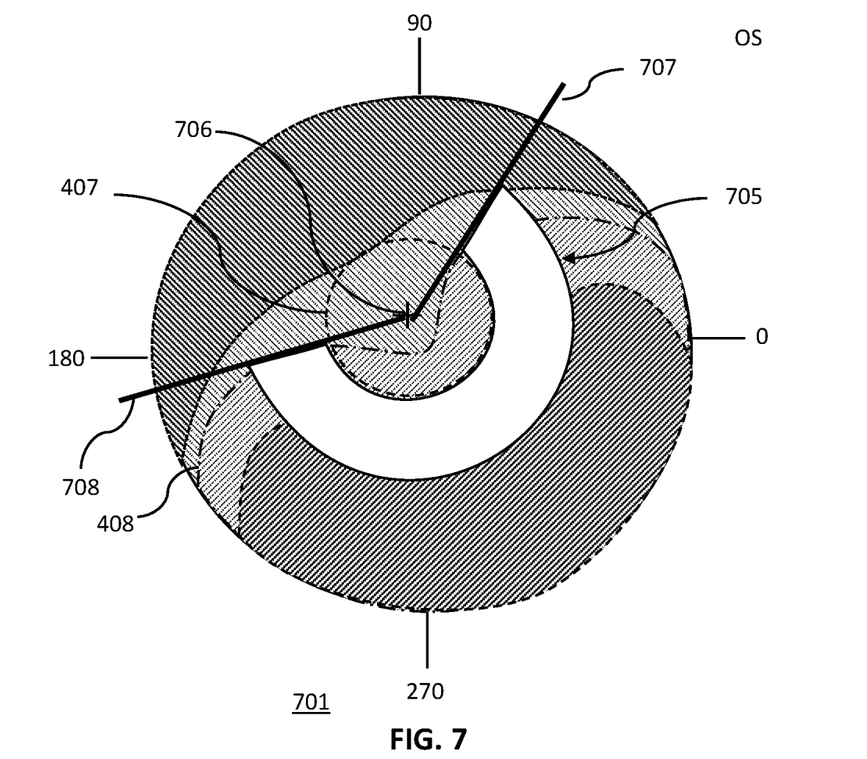
FIG. 7 shows a schematic representation of a first type of corneal augmentation overlaid on an elevation map of a cornea.

FIG. 7 shows a schematic representation 701 of a first type of arcuately shaped corneal augmentation 705 overlaid on an elevation map of a cornea.

In addition to elements of the elevation map of a cornea already depicted in FIG. 4, such as, but not limited to, the zero deviation iso-elevation line 408 and the circle 407 representing a cone of a keratoconus, FIG. 7 shows a location of a thinnest point 706 of the keratoconus. The diameter of the circle 407 representing a cone of a keratoconus may be measured through the thinnest point 706 of a keratoconus. Also shown is a first line 707 that may be tangential to a zero iso-elevation line and passes through the thinnest point, or maximum elevaltion, 706 of a keratoconus. There is also a second line 708 that may be tangential to a zero iso-elevation line and pass through the thinnest point 706 of the keratoconus. As shown, first line 707 is located at approximately 65 degrees and second line 708 is located at approximately 185 degrees.

As shown in FIG. 7, the corneal augmentation 705 is arcuately shaped, having an arc length that may be equal to the arc length of the depressed region of the cornea as revealed by the elevation map of the cornea. As shown in this plan view, the corneal augmentation has an inner, concave curve shaped to partially surround the cone of the keratoconus and an outer, convex curve shaped to fit within an outer ring of an iris associated with the cornea.

Figure 8:
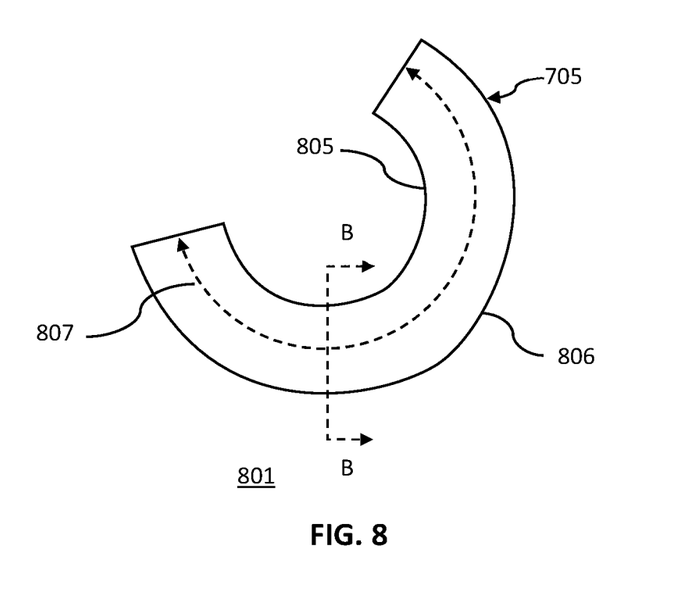
FIG. 8 shows a schematic plan view of a first type of corneal augmentation.

FIG. 8 shows a schematic plan view 801 of a first type of corneal augmentation 705.

As shown in FIG. 8, the corneal augmentation 705 has an inner surface 805 that is concave and shaped to partially surround a cone of keratoconus, and an outer surface 806 that is convex and shaped to fit within an outer ring of an iris associated with said cornea.

In a preferred embodiment, the inner, circular surface may have a radius equal to half the width of a keratoconus cone of the cornea. The width of the keratoconus cone is preferably measured using a tangential topography map of cornea on a line passing through the thinnest point of said keratoconus cone. The outer, circular surface may be concentric with the inner, circular surface and have a radius in a range of 3.75 to 4.25 mm.

Figure 9:
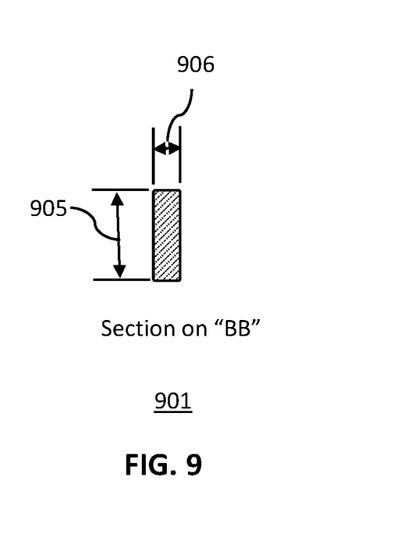
FIG. 9 shows a schematic cross-section taken on "BB" of FIG. 8.

FIG. 9 shows a schematic cross-section 901 taken on "BB" of FIG. 8.

As shown in FIG. 9, the corneal augmentation has a width 905 and a thickness 906.

In a preferred embodiment, the arcuately shaped corneal augmentation may have uniform, rectangular cross-section with a thickness that may be proportional to a maximum keratometry, K-max, of the cornea.

For instance, a satisfactory relationship between the maximum thickness of the corneal augmentation and the maximum keratometry, K-max, has been determined through experience to be that represented in Table 1.

TABLE 1

Maximum thickness of collagen augmentation in μm verses maximum keratometry measured in Diopters.

| Tissue Thickness (μm) | Maximum Keratometry (Diopters) |
|---|---|
| 100-200 | 45-50 |
| 200-250 | 50-55 |
| 250-300 | 55-60 |
| 300-350 | 60-65 |
| 350-400 | 65-70 |
| 400-450 | 70-75 |
| 450-500 | >75 |

The values in Table 1 may be approximated by the equation:

$$t = 10 \times K\text{-max} - 300 \qquad (1)$$

where t represents the maximum thickness in μm, and K-max represents the maximum keratometry in diopters.

In a preferred embodiment, the corneal augmentation may be designed to be located centered on the keratoconus cone of said cornea, and at a depth in a range of 190 μm to 210 μm within the cornea. Furthermore, the inner concave curve may be designed to be located less than 3 mm from the center of a pupil associated with the cornea and at a distance greater than 2 mm from a thinnest point of the keratoconus cone.

Figure 10:
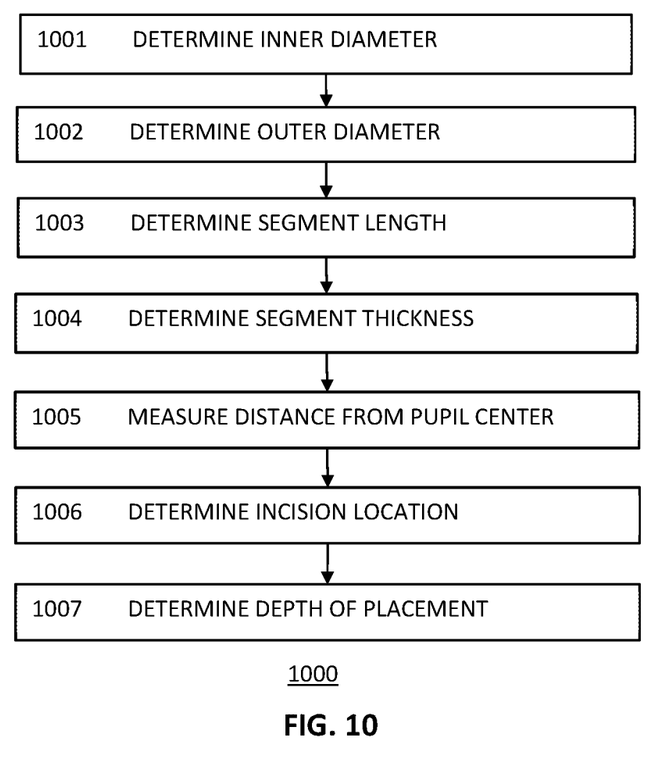
FIG. 10 is a flow diagram showing representative steps of producing and inserting a corneal augmentation of one embodiment of the present invention.

FIG. 10 shows a flow diagram 1000 showing representative steps of producing and inserting a corneal augmentation of one embodiment of the present invention.

In Step 1001 "DETERMINE INNER DIAMETER", the inner diameter of the augmentation may be determined as being equal to, or slightly larger than, the width of the cone of the keratoconus. This may, for instance, be measured using a tangential topography map. The width is typically measured through the thinnest point of the cornea.

In Step 1002 "DETERMINE OUTER DIAMETER", the outer diameter of the augmentation may be determined. This is typically set to 8 mm, though it may be adjusted to avoid placing the augmentation through any peripheral cornea pathology such as, but not limited to, neovascularization or scarring or to avoid the limbus or sclera. The diameter is, however, typically in a range of 6 mm to 9 mm.

In Step 1003 "DETERMINE SEGMENT LENGTH" the length of the augmentation may be determined from a corneal elevation map. The elevation map may be created relative to a best fit sphere, though elevation maps may also be generated relative to other suitable ideal corneal surfaces such as, but not limited to, ellipsoids or toric ellipsoids. In a preferred embodiment, the elevation map may be determined relative to the apex of the keratoconus of the cornea. This may be used to demarcate the depressed area of the cornea which may be elevated, postoperatively, by the corneal augmentation.

In Step 1004 "DETERMINE SEGMENT THICKNESS" the thickness of the augmentation may be determined. The maximum keratometry is the point of steepest curvature on the cornea and may be used as a proxy for the severity of the keratoconus. The maximum keratometry has an inverse relationship with the desired flattening, i.e., the steeper the cornea, the more the desired flattening. A normal human cornea has a focusing power of approximately 40 diopters. The thickness of the augmentation may, therefore, be selected to attempt to return the cornea's focusing power closer to this value. A table of the expected flattening is shown below.

TABLE 2

Approximate expected flattening versus augmentation thickness.

| Maximum Keratometry (D) | Tissue Thickness (μm) | Expected Max Flattening (D) (Approximate) |
|---|---|---|
| 45-48 | 150-200 | 3D-6D |
| 48-52 | 200-250 | 6D-9D |
| 52-55 | 250-300 | 9D-11D |
| 55-60 | 300-350 | 11D-13D |
| 60-65 | 350-400 | 13D-15D |
| 65-70 | 400-450 | 15D-17D |
| >70 | 450-500 | >16D |

In Step 1005 "MEASURE DISTANCE FROM PUPIL CENTER" the location of the edge of the cone from center of the pupil may be measured. These measurements may be used to ensure that the corneal augmentation is placed centered on the cone rather than on the pupil. The location of the edge of the cone may, for instance, be measured in three or more directions such as, but not limited to, temporally, inferotemporally, inferiorly, and nasally.

In Step 1006 "DETERMINE INCISION LOCATION" a determination may be made as to where to make an incision for inserting the corneal augmentation. Typically, the incision is made in the temporal of superior quadrant of the cornea approximately 15 degrees away from where the edge of the corneal augmentation will be located.

In Step 1007 "DETERMINE DEPTH OF PLACEMENT" a decision as to how deep in the cornea the augmentation may be placed. Typically a corneal augmentation of the present invention may be placed at a depth of approximately 200 μm below the anterior surface of the cornea.

Figure 11:
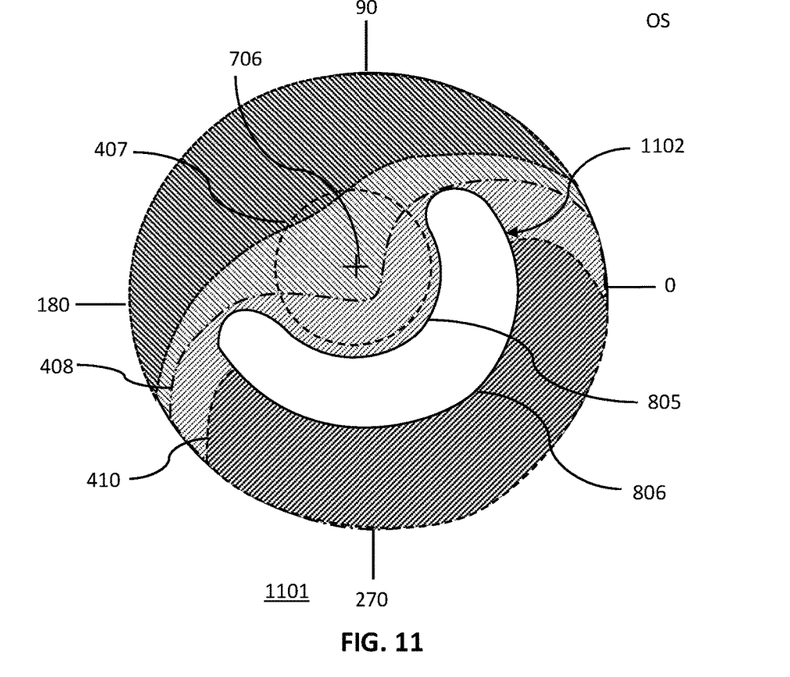
FIG. 11 shows a schematic plan view of a second type of corneal augmentation superimposed on an elevation map of a cornea.

FIG. 11 shows a schematic plan view 1101 of a second type of corneal augmentation 1002 superimposed on an elevation map of a cornea.

The second type of arcuately shaped corneal augmentation 1102 may have an arc length equal to an arc length of a depressed region of the cornea as revealed by an elevation map of the cornea.

As shown in plan view in FIG. 11, the arcuately shaped corneal augmentation 1102 may have an inner surface 805 that may be a concave curve shaped to partially surround a cone 407 of said keratoconus, and an outer surface 806 that may be convex curve shaped to fit within an outer ring of an iris associated with the cornea.

Moreover, the inner surface 805 of the augmentation may be shaped to be, in part, parallel to a first iso-elevation line 408 of said elevation map while the outer concave, curve 806 may be shaped to be, in part, parallel to a second iso-elevation line of the elevation map.

The second type of corneal augmentation 1102 may also be designed to have a thickness that may be proportional to a maximum keratometry of the cornea while being located centered on the keratoconus cone 407 of the cornea, and at a depth in a range of 190 μm to 210 μm within the cornea.

Figure 12:
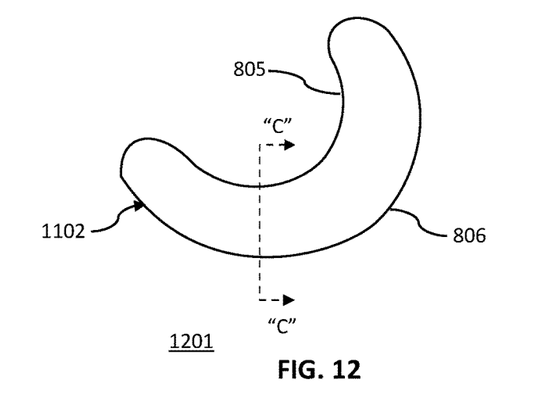
FIG. 12 shows a schematic plane view of a second type of corneal augmentation.

FIG. 12 shows a schematic plane view 1201 of a second type of corneal augmentation 1102.

The arcuately shaped corneal augmentation 1102 may have an inner surface 805 that may be a concave curve shaped to partially surround a cone 407 of said keratoconus, and an outer surface 806 that may be convex curve shaped to fit within an outer ring of an iris associated with the cornea.

Figure 13:
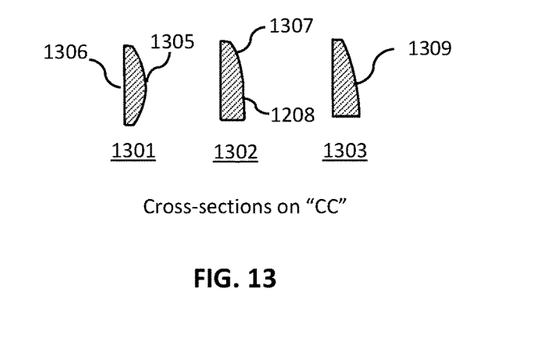
FIG. 13 shows schematic cross-sections of various embodiments of a second type of corneal augmentation.

FIG. 13 shows schematic cross-sections of various embodiments of a second type of corneal augmentation 1102.

The schematic cross-section 1301 shows a first embodiment of a second type of corneal augmentation 1102, with the cross-section being taken on the line "CC" of FIG. 12. The cross-section may, for instance, have a symmetric convex upper surface 1305 and a flat lower surface 1306. The thickness of the second type of corneal augmentation may, therefore, vary. In one embodiment, the peak thickness may be proportional to K-max and be obtained from Table 1, or the associated equation 1.

The thickness may also be customized using empirically calculated weighting functions. For instance, the thickness may be proportional to a weighted product of the maximum keratometry, K-max, and a weighted ratio of a local elevation and a maximum elevation, with the elevations being the difference between an anterior surface of the cornea and a best fit sphere as revealed by a suitable elevation map.

The thickness may, for instance, be calculated using an equation such as:

$$t(x,y) = (10 \times K\text{-max} - 300) \times [[w(x,y) \times e(x,y)]/e\text{max}]] \qquad (2)$$

where t(x,y) represents the thickness in μm at a point (x,y), K-max represents the maximum keratometry measured in diopters, e(x, y) represents the elevation at a Cartesian point (x,y), emax represents the maximum elevation, and w(x,y) represents a weighting function at a point (x,y).

The weighting function, w(x,y) may, for instance, be obtained from numerical simulations and/or an AI program such as, but not limited to, a suitably programmed machine learning system with access to suitable training data which may be empirically collected data or data from numerical simulations or some combination thereof. The computer simulations may, for instance, be a series of "before and after" simulations, i.e., a simulation of an abnormality of the cornea coupled to a series of simulated outcomes using different augmentations.

Alternatively, the weighting functions, w(x,y) may be obtained from a numerical simulation that may be an optimization routine in which the weighting functions are varied to produce a desired outcome in a manner analogous to the optimization of optical systems or the training of machine learning systems using, for instance, a form of gradient descent optimization.

In either case, the simulation may be of the performance of the entire eye, i.e., the optical performance including all the optically relevant structure of the eye such as, but not limited to, the lens, the anterior chamber, and the vitreous body.

The schematic cross-section 1302 shows a second embodiment of a second type of corneal augmentation. In such an embodiment, the upper surface of the augmentation may have a first curved portion 1307 followed by a second flat portion 1308. The first curved portion 1307 may for instance curve up to reach a thickness that may be determined by K-max per Table 1 or equation 1. A reason for having the outer surface thicker may be that the corneal augmentation may ameliorate the corneal disorder not merely by filling the depression gap, but also by tensioning the anterior surface of the cornea.

The schematic cross-section 1303 show a third embodiment of a second type of corneal augmentation 1102. In such an embodiment, the upper surface of the augmentation may have a curved surface 1309 that allows a continuous increase in the thickness of the augmentation with increasing distance from the center of the pupil. The final thickness of the augmentation may, for instance, be the thickness determined by K-max as shown in Table 1 or obtained using equation 1.

Figure 14:
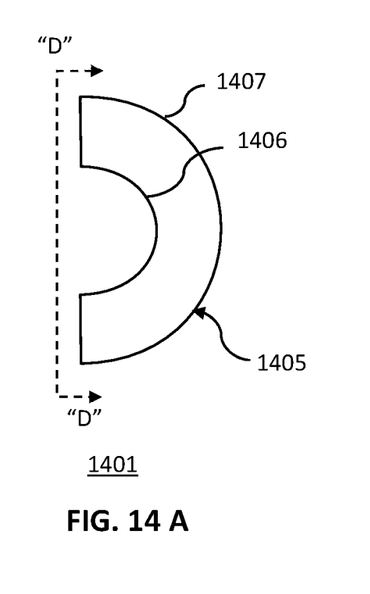
FIG. 14A shows a schematic plane view of a C-shaped corneal augmentation of one embodiment of the present invention.
FIG. 14B shows a schematic end-view of a C-shaped corneal augmentation of one embodiment of the present invention.

FIG. 14A shows a schematic plane view 1401 of a C-shaped corneal augmentation of one embodiment of the present invention.

The C-shaped corneal augmentation 1405 may have an inner circular radius 1406 and a concentrically located outer circular radius 1407. The inner circular radius 1406 may, for instance, be sized to be equal to or slightly larger than half the width of the keratoconus cone so that it may be located to surround it. The outer circular radius 1407 may, for instance, be approximately 4 mm.

FIG. 14B shows a schematic end-view 1402 of a C-shaped corneal augmentation of one embodiment of the present invention.

Figure 15:
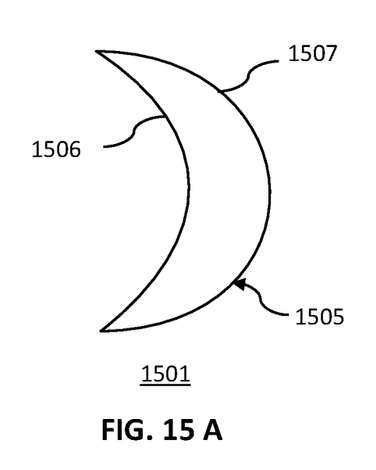
FIG. 15A shows a schematic plane view of a crescent-shaped corneal augmentation of one embodiment of the present invention.
FIG. 15B shows a schematic plane view of a horn shaped corneal augmentation of one embodiment of the present invention.

FIG. 15A shows a schematic plane view 1501 of a crescent shaped corneal augmentation of one embodiment of the present invention.

The crescent shaped corneal augmentation 1505 may have an inner surface 1506 and an outer surface 1507. The inner surface 1506 and the outer surface 1507 may, for instance, both be sectors of a circle of different radii or they may be segments of a suitable curve such as, but not limited to, a parabola or an ellipse. The size of the surfaces may be selected so that the inner surface 1506 surrounds the cone of a keratoconus.

FIG. 15B shows a schematic plane view 1502 of a horn shaped corneal augmentation of one embodiment of the present invention.

The horn shaped corneal augmentation 1510 may have an inner surface 1511 and an outer surface 1512. The inner surface 1511 and the outer surface 1512 may, for instance, both be segments of circles of different radii with the centers offset vertically.

Figure 16:
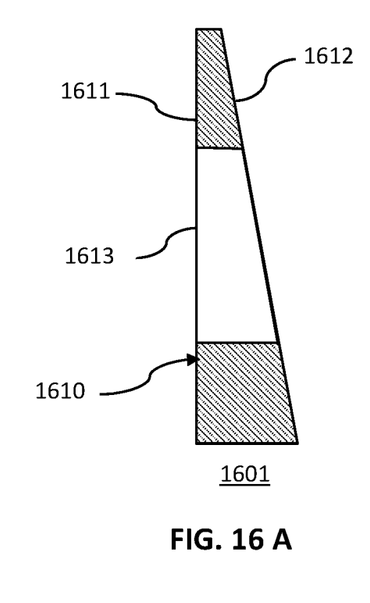
FIG. 16A shows a schematic cross-section of a wedge-shaped corneal augmentation of one embodiment of the present invention.
FIG. 16B shows a schematic cross-section of a trapezoidal-shaped corneal augmentation of further embodiment of the present invention.
FIG. 16C shows a schematic cross-section of a corneal augmentation of another embodiment of the present invention.
FIG. 16D shows a schematic cross-section of a corneal augmentation of yet another embodiment of the present invention.
FIG. 16E shows a schematic cross-section of a corneal augmentation of a further embodiment of the present invention.
FIG. 16F shows a schematic cross-section of a corneal augmentation of still further embodiment of the present invention.

FIG. 16A shows a schematic cross-section 1601 of a wedge-shaped corneal augmentation 1610 of one embodiment of the present invention.

The wedge-shaped corneal augmentation 1610 may, for instance, have a flat lower surface 1611 and an upper sloping surface 1612. Together the flat lower surface 1611 and the upper sloping surface 1612 form a wedge. The degree of angling of the wedge may, for instance, be adjusted depending on the severity of the keratoconus that may, for instance, be characterized in part by the K-max value. An opening 1613 in the corneal augmentation may be sized to be equal to, or slightly larger than the cone of the keratoconus.

FIG. 16B shows a schematic cross-section 1602 of a trapezoidal-shaped corneal augmentation 1615 of one embodiment of the present invention.

The trapezoidal-shaped corneal augmentation 1615 may, for instance, have a flat lower surface 1611, a flat upper surface 1616 and be characterized by a chamfered edge 1617. An opening 1613 in the corneal augmentation may be sized to be equal to, or slightly larger than the cone of the keratoconus.

FIG. 16C shows a schematic cross-section 1603 of a corneal augmentation of another embodiment of the present invention.

The corneal augmentation 1620 of FIG. 16C is characterized by that in addition to a flat lower surface 1611 and a flat upper surface 1616 it may have a dome shaped opening 1621. The dome shaped opening 1621 may, for instance, add structural integrity to the corneal augmentation.

FIG. 16D shows a schematic cross-section 1604 of a corneal augmentation of yet another embodiment of the present invention.

The corneal augmentation 1625 of FIG. 16D may be characterized in that although it may have a flat lower surface 1611 and a flat upper surface 1616 it may have a truncated opening 1627. The truncated opening 1627 may have a thin membrane 1626. The thin membrane 1626 may provide additional structural integrity or, in the case of an onlay augmentation, it may provide an additional barrier.

FIG. 16E shows a schematic cross-section 1605 of a corneal augmentation of a further embodiment of the present invention.

The corneal augmentation 1630 of FIG. 16E may be characterized in that, in addition to a flat upper surface 1616 and an opening 1613 in the corneal augmentation, it may have a curved lower, or posterior, surface 1631. In an onlay augmentation, the curved lower, or posterior, surface 1631 may be shaped to match the anterior surface of the cornea, thereby proving a closer fit.

FIG. 16F shows a schematic cross-section 1606 of a corneal augmentation of still further embodiment of the present invention.

The corneal augmentation 1635 of FIG. 16F may be characterized in that, in addition to a flat lower surface 1611 and an opening 1613 in the corneal augmentation, it may have a curved upper, or anterior, surface 1636.

Figure 17:
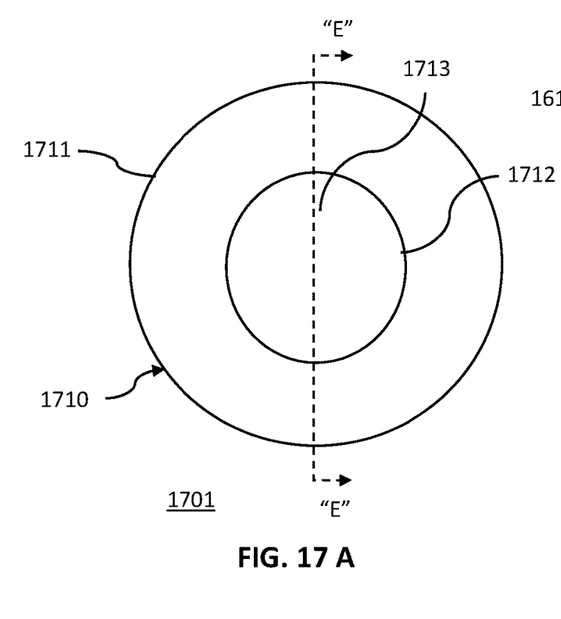
FIG. 17A shows a schematic plane view of a doughnut-shaped corneal augmentation of one embodiment of the present invention.
FIG. 17B shows a schematic cross-section of a doughnut-shaped corneal augmentation of one embodiment of the present invention.
FIG. 17C shows a schematic plane view of another doughnut-shaped corneal augmentation of one embodiment of the present invention.
FIG. 17D shows a schematic plane view of a yet another doughnut-shaped corneal augmentation of one embodiment of the present invention.
FIG. 17E shows a schematic plane view of a lenticularly-shaped corneal augmentation having no central cutout of one embodiment of the present invention.

FIG. 17A shows a schematic plane view 1701 of a doughnut-shaped corneal augmentation 1710 of one embodiment of the present invention.

The doughnut-shaped corneal augmentation 1710 may be characterized in that it has a circular outer surface 1711 and a circular inner surface 1712 that forms a through hole 1713. In a preferred embodiment, the circular outer surface 1711 and the circular inner surface 1712 may be concentric.

FIG. 17B shows a schematic cross-section 1702 of a doughnut-shaped corneal augmentation of one embodiment of the present invention.

As shown in the cross-section, the doughnut-shaped corneal augmentation may have a flat lower surface 1611 and a flat upper surface 1616 with a through hole 1713.

FIG. 17C shows a schematic plane view 1703 of a further doughnut-shaped corneal augmentation of one embodiment of the present invention.

The doughnut-shaped corneal augmentation 1715 of FIG. 17C may be characterized in that although the circular inner surface 1712 may be concentric with the circular outer surface 1711, the diameter of the circular inner surface 1712 relative to the diameter of the circular outer surface 1711 is much smaller than that shown in FIG. 17A. The resultant, relatively smaller through hole 1713 may be suitable for a less severe keratoconus.

FIG. 17D shows a schematic plane view 1704 of a yet another doughnut-shaped corneal augmentation of one embodiment of the present invention.

The doughnut-shaped corneal augmentation 1720 of FIG. 17D may be characterized in that the circular inner surface 1712, and therefore the through hole 1713, are not aligned to be concentric with the circular outer surface 1711. Such an arrangement may, for instance, be appropriate when a cone of a keratoconus may be significantly off set from the pupil.

FIG. 17E shows a schematic plane view 1705 of a lenticularly-shaped corneal augmentation having no central cutout of one embodiment of the present invention. This embodiment may be characterized in that the augmentation 1716 of FIG. 17E is a lenticule with no central cut out.

Figure 18:
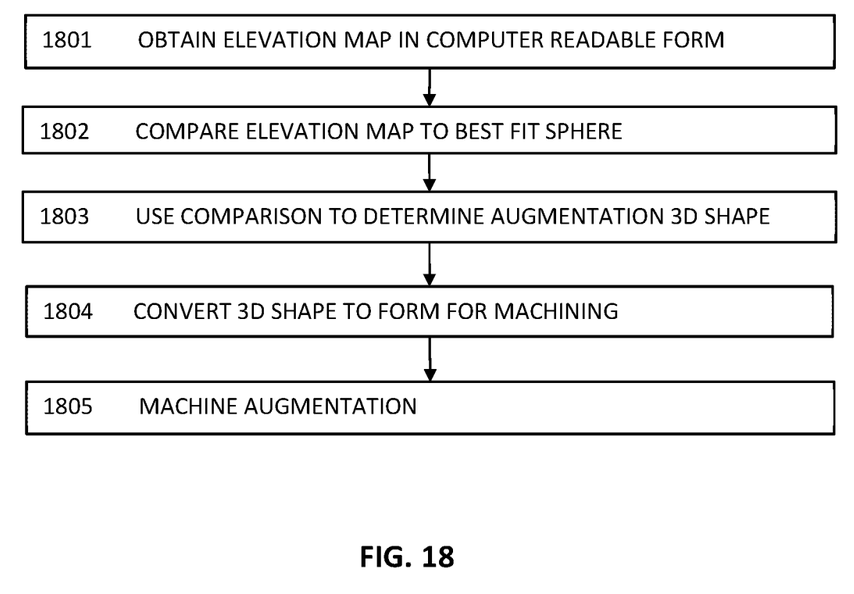
FIG. 18 is a flow diagram showing representative steps of producing a corneal augmentation of one embodiment of the present invention.

FIG. 18 is a flow diagram showing representative steps of producing a corneal augmentation of one embodiment of the present invention.

In Step 1801 "OBTAIN ELEVATION MAP IN COMPUTER READABLE FORM" data may be output from, for instance, a Pentacam™ manufactured by OCULUS Optikgerate GmbH in Wetzlar, Germany, in the form of an elevation map of the cornea. The elevation map may, for instance, be output as heights in μm on a cartesian grid. The output may be a list of such values in a suitable computer readable format such as, but not limited to, as comma separated values, i.e., as a .cvs file.

In Step 1802 "COMPARE ELEVATION MAP TO BEST FIT SPHERE" the elevation map obtained in Step 1802 may be compared to a surface representing a desired shape of the cornea such as, but not limited to, a best fit sphere, or a best fit spherical toroid. The comparison may be performed by suitable software such as, but not limited to, software modules written in a suitable multi-paradigm programing language such as, but not limited to, MathWorks MATLAB™.

In Step 1803 "USE COMPARISON TO DETERMINE AUGMENTATION 3D SHAPE" the comparison between an elevation map and a best fit sphere may be used to determine the desired shape of a 3D augmentation. The desired shape may, for instance, be a shape that fills the region where an anterior surface of a cornea is depressed with respect to the best fit sphere. Such a shape is indicated, for instance, as shaded region 405 in FIG. 6.

In Step 1804 "CONVERT 3D SHAPE TO FORM FOR MACHINING" the desired 3D shape obtained in Step 1803 may be converted into a form suitable for forwarding to a suitable manufacturing machine such as, but not limited to, a 3D CAM milling machine or an additive manufacturing facility such as, but not limited to, a 3D printing machine. A suitable format for expressing the desired 3D shape may, for instance, be the stereolithography file format (STL) in which the surface of the desired 3D augmentation may be represented as a series of connected triangles.

In Step 1805 "MACHINE AUGMENTATION" the desired 3D augmentation shape may be formed form a corneal template by means of a computer driven milling machine using the STL file generated in Step 1805. One of ordinary skill in the art may appreciate that the desired shape may be expressed in other suitable CAD/CAM file formats such as, but not limited to, STEP, or AutoCAD DXF.

Although this invention has been described with a certain degree of particularity, it is to be understood that the present disclosure has been made only by way of illustration and that numerous changes in the details of construction and arrangement of parts may be resorted to without departing from the spirit and the scope of the invention.

What is claimed:

1. A customized device for the amelioration of an abnormality of a cornea, comprising:
 a corneal augmentation produced from a corneal template comprised of corneal tissue, said production comprising:
 measuring a severity of said cornea;
 obtaining a corneal map quantifying a deviation of said abnormal cornea from an optimal corneal shape;

calculating a suitable three-dimensional shape of said corneal augmentation using said measure of severity of said abnormality and said corneal map; and, shaping said corneal template to said three-dimensional shape.

2. The customized device of claim 1, wherein, said corneal template comprised of corneal tissue is obtained from a source other than the cornea being treated and is one of a corneal allograft, a corneal xenograft, a manufactured corneal tissue or a bioengineered corneal tissue.

3. The customized device of claim 1, wherein, said corneal map is an elevation map, said measure of severity of said abnormality is a maximum keratometry of said cornea, and said corneal augmentation is disc shaped, having:
a non-uniform cross-section; and,
a maximum thickness proportional to said maximum keratometry of said cornea.

4. The customized device of claim 3, wherein, said maximum thickness is determined using the equation:

$$t=10 \times K\text{-max}-300,$$

where t represents the maximum thickness in μm, and K-max represents the maximum keratometry measured in diopters.

5. The customized device of claim 3, further comprising a circularly shaped through hole.

6. The customized device of claim 1, wherein, said corneal augmentation is arcuately shaped.

7. The customized device of claim 6, wherein, said corneal map is an elevation map, said measure of severity of said abnormality is a maximum keratometry of said cornea, and said corneal augmentation is arcuately shaped, having:
an arc length equal to an arc length of a depressed region of said cornea as revealed by said elevation map of said cornea;
a thickness proportional to said maximum keratometry of said cornea;
in plan view, an inner, concave curve shaped to partially surround a cone of said keratoconus; and,
in plan view, an outer, convex curve shaped to fit within an outer edge of said cornea.

8. The customized device of claim 7, wherein, said elevation map used to reveal said depressed region of said cornea is determined as a difference between a best fit sphere relative to an apex of said keratoconus and the anterior surface of said cornea.

9. The customized device of claim 7, wherein, said arcuately shaped corneal augmentation is further defined by having:
a uniform, rectangular cross-section with a thickness proportional to said maximum keratometry of said cornea;
an inner, circular surface with a radius equal to half the width of a keratoconus cone of said cornea; and,
an outer, circular surface, concentric with said inner, circular surface, with a radius in a range of 3 to 4.5 mm.

10. The customized device of claim 9, wherein, said thickness is determined using the equation:

$$t=10 \times K\text{-max}-300,$$

where t represents the maximum thickness in μm, and K-max represents the maximum keratometry measured in diopters.

11. The customized device of claim 10, wherein, said width of said keratoconus cone is measured using a tangential topography map of said cornea.

12. The customized device of claim 11, wherein, said width of said keratoconus cone is measured on a line passing through a thinnest point of said keratoconus cone.

13. The customized device of claim 12, wherein, said corneal augmentation is designed to be located centered on said keratoconus cone of said cornea, and at a depth in a range of 190 μm to 210 μm within said cornea.

14. The customized device of claim 13, wherein said inner concave curve is designed to be located less than 3 mm from said center of said pupil and greater than 2 mm from a thinnest point of said keratoconus cone.

15. The customized device of claim 7, wherein, in a plan view, said inner concave, curve is further shaped to be, in part, parallel to a first iso-elevation line of said elevation map; and
in a plan view, said outer concave, curve is further shaped to be, in part, parallel to a second iso-elevation line of said elevation map.

16. The customized device of claim 15, wherein, said thickness is proportional to a weighted product of said maximum keratometry and a weighted ratio of a local elevation and a maximum elevation.

17. The customized device of claim 16, wherein said thickness is given by the equation:

$$t(x,y)=(10 \times K\text{-max}-300) \times [[w(x,y) \times e(x,y)]/e\text{max}]]$$

where t(x,y) represents the thickness in μm at a point (x,y), K-max represents the maximum keratometry measured in diopters, e(x, y) represents the elevation at a point (x,y), emax represents the maximum elevation, and w(x,y) represents a weighting function at a point (x,y).

18. A method of producing and using a custom device for the amelioration of a cornea exhibiting keratoconus, comprising:
forming a corneal tissue template into an arcuately shaped corneal augmentation having:
an arc length equal to an arc length of a depressed region of said cornea as revealed by an elevation map of said cornea;
a uniform, rectangular cross-section with a thickness proportional to a maximum keratometry of said cornea;
an inner, circular surface with a radius equal to half the width of a keratoconus cone of said cornea; and,
an outer, circular surface, concentric with said inner, circular surface, with a radius in a range of 3 to 4.5 mm.

19. The method of producing and using a custom device of claim 18, wherein, said corneal augmentation is located centered on said keratoconus cone of said cornea, and at a depth in a range of 190 μm to 210 μm within said cornea.

20. The customized device of claim 19, wherein said inner surface is located less than 3 mm from said center of said pupil and greater than 2 mm from a thinnest point of said keratoconus cone.

* * * * *